(12) United States Patent
Maleev (10) Patent No.: US 9,182,341 B2
(45) Date of Patent: Nov. 10, 2015

(54) OPTICAL SURFACE SCANNING SYSTEMS AND METHODS

(71) Applicant: KLA-Tencor Corporation, Milpitas, CA (US)

(72) Inventor: Ivan Maleev, Pleasanton, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 0 days.

(21) Appl. No.: 13/916,334

(22) Filed: Jun. 12, 2013

(65) Prior Publication Data

US 2013/0335736 A1    Dec. 19, 2013

Related U.S. Application Data

(60) Provisional application No. 61/659,050, filed on Jun. 13, 2012.

(51) Int. Cl.

| | |
|---|---|
| *G01J 3/42* | (2006.01) |
| *G01N 21/25* | (2006.01) |
| *G01N 21/47* | (2006.01) |
| *G01N 21/95* | (2006.01) |
| *G03F 7/20* | (2006.01) |

(52) U.S. Cl.
CPC .......... *G01N 21/255* (2013.01); *G01N 21/4788* (2013.01); *G01N 21/9501* (2013.01); *G03F 7/70625* (2013.01)

(58) Field of Classification Search
CPC . G01N 21/25; G01N 21/255; G01N 21/4788; G01N 21/9501

USPC ..................................... 356/326, 327, 237.1
See application file for complete search history.

(56) References Cited

U.S. PATENT DOCUMENTS

| | | | |
|---|---|---|---|
| 4,844,617 A | | 7/1989 | Kelderman et al. |
| 5,192,980 A | * | 3/1993 | Dixon et al. .................. 356/326 |
| 5,844,727 A | | 12/1998 | Partlo |
| 6,429,943 B1 | * | 8/2002 | Opsal et al. ................... 356/625 |
| 6,567,584 B2 | | 5/2003 | Carlisle et al. |

(Continued)

FOREIGN PATENT DOCUMENTS

| | | |
|---|---|---|
| EP | 1508772 | 2/1999 |
| WO | 0250509 | 6/2002 |

OTHER PUBLICATIONS

"Diffractive Microoptics" Jenoptik Optical Systems, downloaded from http://www.jenoptik-inc.com/microoptic-solutions/diffractive-optical-elements.html, Sep. 6, 2013, pp. 1-4.

(Continued)

*Primary Examiner* — Gregory J Toatley
*Assistant Examiner* — Maurice Smith
(74) *Attorney, Agent, or Firm* — Meyertons, Hood, Kivlin, Kowert & Goetzel, P.C.; Eric B. Meyertons (57) ABSTRACT

An optical scanning system may include a moving sample positioning stage that supports the sample during an optical measurement of the sample using the light source and the spectrometer. The moving sample positioning stage may move the sample in at least one direction during the optical measurement of the sample. A scatterometer system may include collection imaging optics for imaging the reflected light onto a multi-pixel sensor that collects and analyze the reflected light.

8 Claims, 4 Drawing Sheets

(56) References Cited

U.S. PATENT DOCUMENTS

| | | | |
|---|---|---|---|
| 6,606,173 | B2 | 8/2003 | Kappel et al. |
| 6,671,044 | B2 * | 12/2003 | Ortyn et al. .................... 356/326 |
| 6,999,180 | B1 | 2/2006 | Janik et al. |
| 7,038,776 | B1 | 5/2006 | Ansley et al. |
| 7,121,357 | B1 | 10/2006 | Raimondi |
| 7,456,947 | B2 * | 11/2008 | Kurata ........................ 356/237.2 |
| 7,487,049 | B2 * | 2/2009 | Matsui ............................ 702/40 |
| 7,528,944 | B2 * | 5/2009 | Chen et al. ................. 356/237.6 |
| 7,656,542 | B2 * | 2/2010 | Littau et al. ..................... 356/625 |
| 8,212,995 | B2 | 7/2012 | Koehler et al. |
| 2002/0179867 | A1 * | 12/2002 | Fielden et al. ........... 250/559.45 |
| 2002/0186367 | A1 * | 12/2002 | Eytan et al. ................ 356/237.1 |
| 2003/0048933 | A1 * | 3/2003 | Brown et al. ................. 382/128 |
| 2003/0071227 | A1 * | 4/2003 | Wolleschensky .......... 250/459.1 |
| 2004/0233442 | A1 | 11/2004 | Mieher et al. |
| 2008/0014748 | A1 | 1/2008 | Perry |
| 2008/0144023 | A1 * | 6/2008 | Shibata et al. ............. 356/237.2 |
| 2009/0219491 | A1 | 9/2009 | Williams et al. |
| 2009/0279090 | A1 * | 11/2009 | Wolf et al. .................... 356/369 |
| 2010/0188656 | A1 * | 7/2010 | Matsui et al. .............. 356/237.3 |
| 2010/0188762 | A1 | 7/2010 | Cook |
| 2011/0085221 | A1 | 4/2011 | Ortyn et al. |
| 2013/0077070 | A1 | 3/2013 | Schimmel et al. |

OTHER PUBLICATIONS

"Top Hat Beam Shaper" OSELA INC, downloaded from http://www.oselainc.com/products/top-hat-beam-shaper/, Sep. 6, 2013, p. 1.

Olivier Gilbert, et al "Angle-resolved Ellipsometry of Scattering Patterns from Arbitrary Surfaces and Bulks" 2005 Optical Society of America, pp. 1-16.

Michael W. Kudenov, et al "Fourier Transform Channeled Spectropolarimetry in the MWR" 2007 Optical Society of America, pp. 1-14.

Derek S. Sabatke, et al "Linear Operator Theory of Channeled Spectropolarimetry" 2005 Optical Society of America, pp. 1-10.

International Search Report and Written Opinion from PCT/US2013/045528, dated Sep. 25, 2013, KLA-Tencor Corporation, pp. 1-13.

* cited by examiner

OPTICAL SURFACE SCANNING SYSTEMS AND METHODS

PRIORITY CLAIM

This patent claims priority to U.S. Provisional Patent Application No. 61/659,050 filed Jun. 13, 2012, which is incorporated by reference in its entirety.

BACKGROUND

1. Field of the Invention

The present invention relates to surface scanning systems. More particularly, the invention relates to systems and methods of semiconductor surface scanning using scatterometers.

2. Description of Related Art

Current ellipsometers and reflectometers predominantly use point-to-point stages and so called move-acquire-measure (MAM) process to perform metrology on semiconductor wafers or other scanned surfaces. The "move" portion involves point-to-point motion of a wafer carrying stage, and includes acceleration of the stage, followed by deceleration. Because of practical mechanical limitations imposed on acceleration rate, the typical time to move from point to point cannot be less then a few tens of milliseconds. Once the wafer (sample) is positioned for the optical system to start the next acquisition, the "acquire" portion of the process commences in which the optical system acquires sample data. In the case of polarized measurements, that typically takes at least multiple milliseconds, more if higher sensitivity is desired, and even more if the system has moving parts such as a rotating polarizer and/or an analyzer. The "measure" portion involves data analysis and may commence concurrently with the start of a subsequent MAM cycle. Overall, practical limitations and sensitivity requirements may limit MAM times to hundreds of milliseconds. For example, assuming 200 ms MAM and 300 measurements per wafer sample plan, a single wafer will require 60 seconds to process, which equates to 60 wafers per hour (wph) throughput. Therefore, the practical limit on the number of samples per wafer may be estimated to not exceed ~1000 measurements to allow better than 20 wph throughput.

An advantage of the point-to-point method is the ability to measure within a specified box, which may have dimensions on the order of 10 μm or less. Ellipsometers and reflectometers also have the unique ability to perform non-destructive measurements of film thicknesses, dispersion coefficients (n and k), and critical dimensions of gratings (OCD). While such point-to-point systems provide better sensitivity and the ability to measure specific locations, such systems are also inherently limited by the Move-Acquire-Measure (MAM) time per single measurement. Typical measurement sample plans may not exceed a few tens of locations per wafer to stay within reasonable wafers-per-hour (WPH) throughput range. The limitation in measurement locations (scanning area on the sample) arises because of limited acceleration and speed of a sample moving system (the overhead between sample measurements) in combination with the time to make the actual measurement on the sample (e.g., time for point-to-point data acquisition). Thus, it may be beneficial for a semiconductor manufacturer to have a complete map of a wafer without sacrificing throughput.

Alternatives to the point-to-point systems are systems that record all necessary signals simultaneously with the quality of the signal limited by exposure time. U.S. Pat. No. 7,121, 357 to Meeks, which is incorporated by reference as if fully set forth herein, discloses an example of such a system. Such systems would predominantly make measurements in a given location on a wafer with the wafer shift (during measurement) similar or less than the optical spot size. The wafer shift being similar or less than the optical spot size, however, limits the mapping size on the wafer for data acquisition. In addition, simultaneously recording all the signals may put severe restrictions on available engineering solutions. For example, rotating polarizer/analyzer/compensator ellipsometers (RPE/RAE/RCE) and their combinations may be excluded from being used in a system that records all necessary signals simultaneously because they are non-simultaneous measurement systems. RPE/RAE/RCE ellipsometers, however, provide best-in-class sensitivity. Future demands for higher sensitivity may require the use of additional Mueller matrix elements, which would further increase the desire for using non-simultaneous measurement systems while providing higher scanning system throughput.

It may also be desired for a scanning system to provide capability to collect specular reflection order information from a sample via multiple channels. Collecting specular reflection order information via multiple channels may provide improved sensitivity, improved throughput, and possibly provide the ability to resolve small features on the wafer. In addition, small surface defects, such as scratches, may be detectable.

U.S. Pat. Appl. Pub. No. 2008/0014748 to Perry, which is incorporated by reference as if fully set forth herein, describes a multichannel reflectance analyzing system that relies on a bundle of fibers. A problem in the disclosed multichannel reflectance analyzing system is that it relies on a bundle of intermixed illumination and collection fibers. It may be implemented in two ways. A first way of implementation is imaging the sample surface on the fiber entrance. Since collection fibers constitute only a portion of the bundle, however, the system will only provide a subset of surface information and would not be suitable for detection of surface defects. That behavior may be suitable for the applications described in the application but would not be acceptable for a wafer inspection system. A second way of implementation is defocusing the system. When the system is defocused, however, the optical throughput suffers and the system may not provide desired surface resolution (e.g., the system may not be sensitive to surface defects).

SUMMARY

In certain embodiments, an optical scanning system includes a light source that provide slight towards a sample, a spectrometer that collects light reflected from the sample, and a moving sample positioning stage that supports the sample during an optical measurement of the sample using the light source and the spectrometer. The moving sample positioning stage may move the sample in at least one direction during the optical measurement of the sample. In some embodiments, the moving sample positioning stage rotates the sample during the optical measurement of the sample. In some embodiments, a continuous auto-focus system maintains focus of the light on the sample during the optical measurement of the sample. In certain embodiments, the sample is moved a distance larger than an optical beam spot size of the light on the sample during the optical measurement.

In certain embodiments, a method for providing an optical measurement from a sample includes providing light from a light source towards a sample, collecting light reflected from the sample using a spectrometer, obtaining an optical measurement of the sample using the light source and the spectrometer, and moving the sample in at least one direction during the optical measurement by moving a sample positioning stage that supports the sample.

In certain embodiments, a scatterometer system includes a light source that provides light incident on a sample, a sample positioning stage that supports the sample during an optical measurement of the sample, and collection imaging optics for imaging the reflected light onto a multi-pixel sensor that collects and analyze the reflected light. In some embodiments, the collection imaging optics includes a prism or variable-over-image-plane optical delay component that recovers a perpendicularity of an image plane to an optical axis in light reflected from the sample at an oblique angle. In some embodiments, the collection imaging optics images light reflected normally, or close to normally, from a surface of the sample onto the multi-pixel sensor. In some embodiments, the collection imaging optics includes a lens or a set of optical surfaces for imaging the reflected light onto the multi-pixel sensor. In some embodiments, the multi-pixel sensor is capable of collecting and providing information about some or all elements of a polarization matrix.

BRIEF DESCRIPTION OF THE DRAWINGS

Features and advantages of the methods and apparatus of the present invention will be more fully appreciated by reference to the following detailed description of presently preferred but nonetheless illustrative embodiments in accordance with the present invention when taken in conjunction with the accompanying drawings in which.

While the invention is susceptible to various modifications and alternative forms, specific embodiments thereof are shown by way of example in the drawings and will herein be described in detail. The drawings may not be to scale. It should be understood that the drawings and detailed description thereto are not intended to limit the invention to the particular form disclosed, but to the contrary, the intention is to cover all modifications, equivalents and alternatives falling within the spirit and scope of the present invention as defined by the appended claims.

DETAILED DESCRIPTION OF EMBODIMENTS

In the context of this patent, the term "coupled" means either a direct connection or an indirect connection (e.g., one or more intervening connections) between one or more objects or components. The phrase "directly connected" means a direct connection between objects or components such that the objects or components are connected directly to each other so that the objects or components operate in a "point of use" manner.

In certain embodiments, a sample or target (e.g., a semiconductor wafer) is moved during optical scanning of the target to provide increased scanning coverage over the sample surface (e.g., scanning over substantially the entire surface of the sample (wafer)). Scattering or reflecting measurements may be taken from the sample while the sample is moved. In some embodiments, the sample is continuously moved while taking the optical (scattering or reflecting) measurements. In certain embodiments, the sample is moved a distance larger than (e.g., substantially larger than) an optical beam spot size of the optical scanning system during data acquisition (e.g., during a time of measurement on the sample by the optical scanning system). Moving the sample such distances during data acquisition provides data (information) averaged over a distance on the sample with different portions of signal collected over substantially different locations on the sample. Moving the sample while taking optical scanning measurements may increase sample coverage (e.g., increase the scanning area) while maintaining throughputs substantially similar to throughputs for current point-to-point scanning systems.

In certain embodiments, the sample is moved using a moving wafer positioning system (e.g., a continuously moving wafer positioning system) in an optical scanning system (e.g., a scanning stage scatterometer). The optical scanning system with the moving wafer positioning system may be based on any ellipsometer or reflectometer architecture known in the art. For example, the optical scanning system may use optical systems and data acquisition systems found in any ellipsometer or reflectometer architecture known in the art. Examples of systems that the optical scanning system may be based on include, but are not limited to, spectroscopic ellipsometers and reflectometers, single-wavelength ellipsometers, angular resolved reflectometers and ellipsometers, and any combination of systems that measure multiple polarization content and reflectivity of a sample at either single or multiple wavelengths, angles of incidence, and angles of reflection/scattering. The optical scanning system may be capable of recording all measurement information (data acquisition) simultaneously or the optical scanning system may be a non-simultaneous measurement system such as a rotating polarizing ellipsometer. In certain embodiments, the optical scanning system uses a continuous auto-focus system in combination with the moving wafer positioning system. The continuous auto-focus system may maintain focus of the light on the sample during optical scanning of the sample.

The moving wafer positioning system may move the sample in different relative directions while the sample is scanned (e.g., while measurements are made or during data acquisition). In certain embodiments, the moving wafer positioning system moves the sample by rotating a stage supporting the sample (e.g., the stage is a scanning RT (rotating and theta)-stage). In some embodiments, the moving wafer positioning system moves the sample by translating the sample in X and Y directions (e.g., using a scanning XY-stage to support the sample). Using a scanning RT-stage may provide increased throughput versus using a scanning XY-stage.

Figure 1:
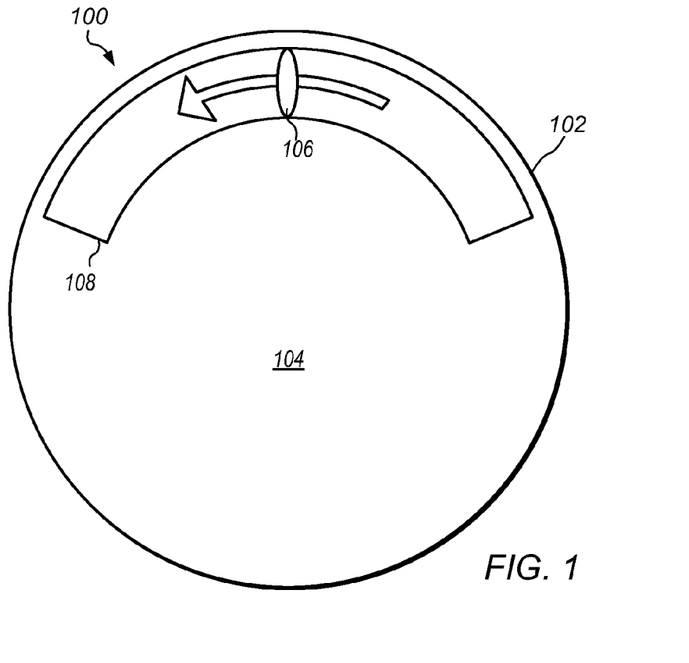
FIG. 1 depicts a top view representation of an embodiment of a stage used in a moving wafer positioning system of an optical scanning system.

FIG. 1 depicts a top view representation of an embodiment of a stage used in a moving wafer positioning system of an optical scanning system. Moving wafer positioning system 100 includes stage 102. Sample 104 is placed on stage 102. Sample 104 may be, for example, a semiconductor wafer. In certain embodiments, stage 102 rotates sample 104 during optical scanning using optical beam spot 106 (e.g., stage 102 is a scanning RT-stage). Optical beam spot 106 may be used by the optical scanning system for scatterometer measurements of sample 104.

In certain embodiments, as shown in FIG. 1, optical beam spot 106 remains fixed while sample 104 moves (rotates) during measurement acquisition by the optical scanning system. Since sample 104 moves during acquisition, a measured signal from optical beam spot 106 is an average over multiple locations on the sample to produce effective measurement spot 108. As an example, optical beam spot 106 may be about 50 μm×20 μm in size (elongated in radial direction). If stage 102 rotates at about 600 rpm, the stage provides a linear speed at the edge of a 300 mm diameter sample 104 (a 300 mm wafer) equal to about 10 m/s. If the optical scanning system is assumed to have an acquisition time of 1 ms (millisecond), sample 104 will move about 1 cm during the acquisition, which produces effective measurement spot 108 with a size of about 50 μm×1 cm. For a 100 ms acquisition time (similar to acquisition time for a rotating polarizing ellipsometer), sample 104 will move 1 m (e.g., the sample will make one full rotation). Conversely, a dedicated scatterometer without moving parts and with a high speed sensor operating at a multiple kHz sampling rate may provide a tangential resolution of 1 mm or less.

Because of the movement of sample 104 during the acquisition time, information about sample surface changes may be collected in the radial direction, which may be limited by the scan pitch. Data collection in the radial direction may be useful for measurements of bow effects on sample 104. In some embodiments, information about sample surface changes are collected in the tangential direction if the sample rotation speed is sufficiently slow and the acquisition time is sufficiently fast. Acquiring information using moving wafer positioning system 100 has little or no overhead related to the motion of stage 102 between measurement points unlike point-to-point scanning systems. Moving wafer positioning system 100 provides an efficient system for acquiring scanning information across a large area of sample 104 (e.g., substantially the entire sample).

Figure 2:
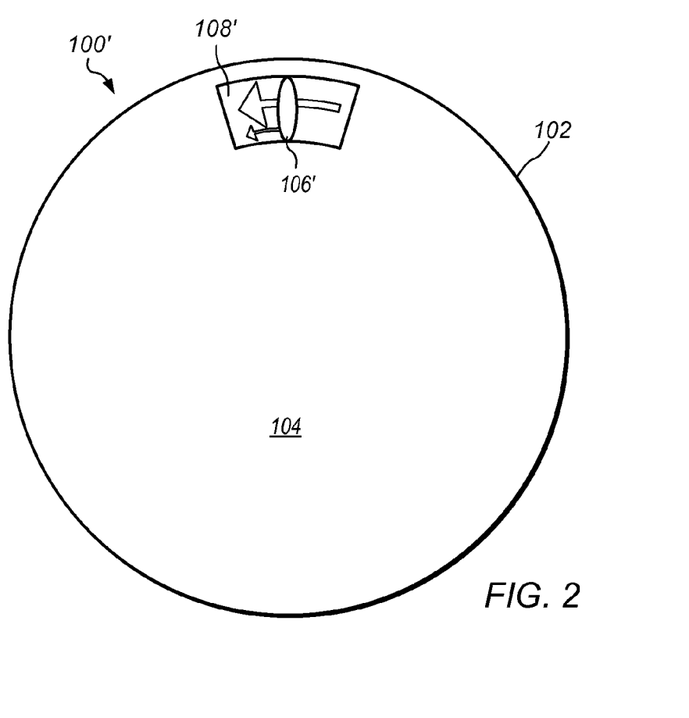
FIG. 2 depicts a top view representation of another embodiment of a stage used in a moving wafer positioning system of an optical scanning system.

FIG. 2 depicts a top view representation of another embodiment of a stage used in a moving wafer positioning system of an optical scanning system. Moving wafer positioning system 100' includes stage 102' with optical beam spot 106' provided by the optical scanning system. In certain embodiments, optical beam spot 106' moves synchronously with stage 102' during measurement acquisition. Thus, optical beam spot 106' illuminates the same location on sample 104 even with the sample moving on stage 102'.

In some embodiments, the optical scanning system uses time-delay integration (TDI) capability to allow optical beam spot 106' to "freeze" (e.g., temporarily freeze) on a specific location on sample 104 while the sample moves. Such an optical scanning system may use a TDI sensor with a large total area. By synchronizing the TDI with motion of stage 102', the target of optical beam spot 106' may effectively "freeze" sensor effective acquisition area 108' on sample 104. Area 108' may move along with sample 104 and allow the optical scanning system to collect data (information) from the same wafer location over a period of time-delays integration (e.g., the time that a target location moves over the total sensor area).

In some embodiments, the size of optical beam spot 106' is relatively similar to sensor effective acquisition area 108' and the beam spot moves as sample 104 moves, following sample target location synchronously with the sensor effective acquisition area. Such embodiments allow for concerted illumination of a specific location on sample 104 with high total signal level and correspondingly higher sensitivity at a subset of (actually illuminated) sample locations. Such embodiments may, however, not sample an entire sample surface.

In some embodiments, the optical beam spot has a size that substantially matches the total area of the sensor in the optical scanning system (e.g., sample 104 is "flooded" with light and the targeted sample location is always illuminated regardless of motion of the sample). "Flooding" may allow for scanning the whole surface of sample 104 at the expense of some sensitivity.

In some embodiments, a large-area solid-state sensor (such as photodiode or PMT) is used instead of the TDI sensor. The solid-state sensor may be used with a moving optical beam spot (such as optical beam spot 106', shown in FIG. 2). In such embodiments, the target sample location moves with respect to the sensor but the target sample location is still registered by the same sensor cell/pixel. The use of the solid-state sensor may be less costly than the use of the TDI sensor and associated optics. The solid-state sensor, however, may not allow the ability to control the size of the effective acquisition area (e.g., effective acquisition area 108' shown in FIG. 2) as the effective acquisition area would be determined by the size of the optical beam spot, which would be tightly controlled due to the use of the solid-state sensor. In some embodiments, collection optics in the optical scanning system are moved and a small area sensor is used in combination with either synchronously moving the optical beam spot with the stage or "flooding" the sample with illumination.

In systems using the TDI sensor and/or the moving optical beam spot, the distance the sample travels during measurement acquisition may be less than the TDI sensor dimension and/or less than the range of the optical beam spot moving system. Limiting the distance the sample travels may limit the total acquisition time per sample and, thus, such systems may be used in scatterometers without moving parts. Such systems, however, may be useful for looking at a specific sample location, which allows sample scans with high resolution in both radial and tangential directions.

Figure 3:
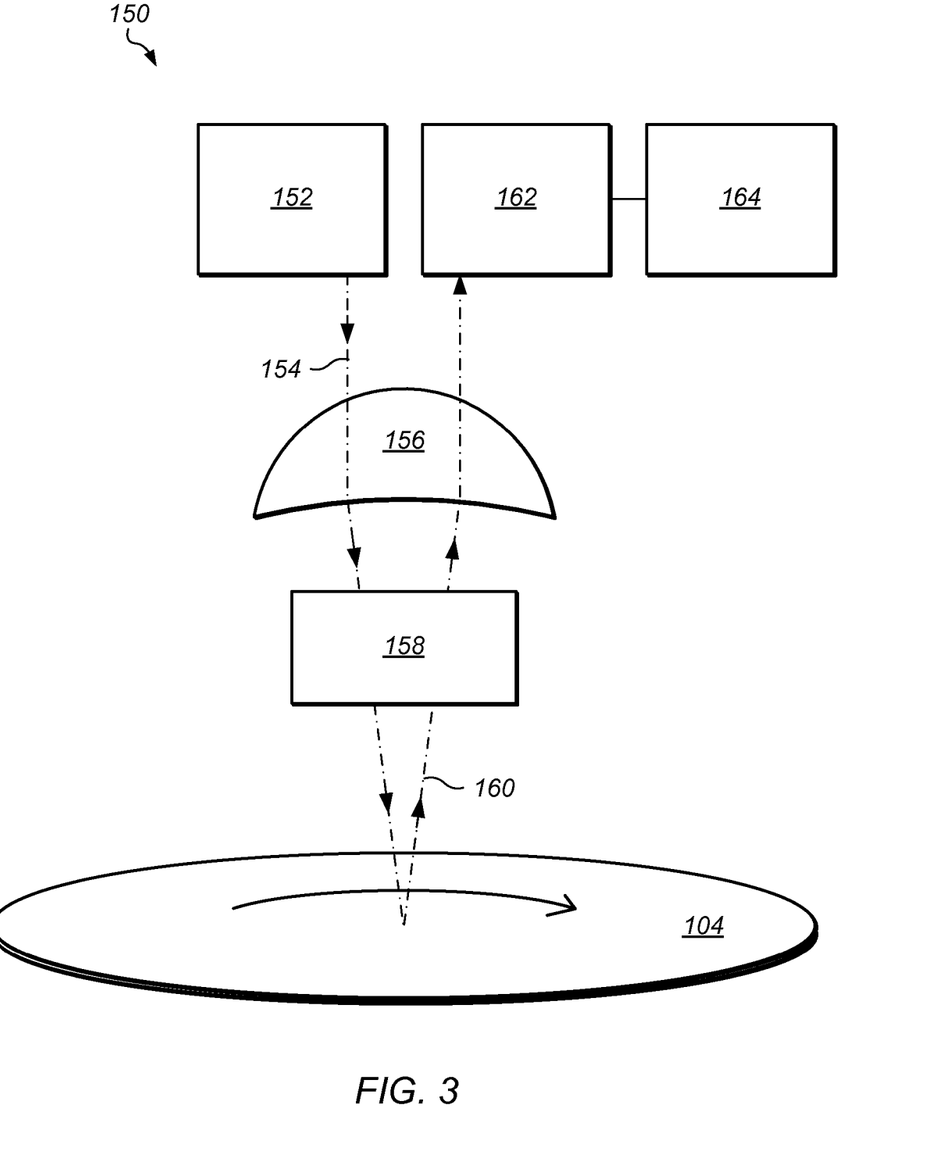
FIG. 3 depicts a representation of an embodiment of an optical scanning system using a polarized light source.

FIG. 3 depicts a representation of an embodiment of an optical scanning system using a polarized light source. Optical scanning system 150 includes moving wafer positioning system 100. Sample 104 may be placed on moving wafer positioning system 100. Light source 152 may be, for example, a broadband light source. Incident light 154 from light source 152 may pass through lens 156 and polarizer 158.

Incident light 154 may reflect off sample 104 as reflected light 160. Reflected light 160 may pass through polarizer 158 and lens 156 before the reflected light is collected in spectrometer 162. Data processing unit 164 may be coupled to spectrometer 162 to collect and analyze information from reflected light 162 to assess surface information of sample 104.

Use of moving wafer positioning system 100 (shown in FIG. 1), or moving wafer positioning system 100' (shown in FIG. 2), in optical scanning system 150 allows full wafer (sample) measurements to be taken at practical throughputs (e.g., about 20 wph to about 100 wph) using traditional scatterometry techniques (e.g., spectroscopic ellipsometry and reflectometry, single-wavelength ellipsometry, or angular-resolved reflectometry and ellipsometry). As compared to point-to-point scanning systems, optical scanning systems using the moving wafer positioning system have little or no overhead related to the motion of the scanning stage between measurement points (e.g., there is no overhead due to moving the wafer (sample) point-to-point between measurements). In addition, optical scanning systems using the moving wafer positioning system allow inclusion of optical designs with higher sensitivities such as rotating-polarizing ellipsometers.

Figure 4:
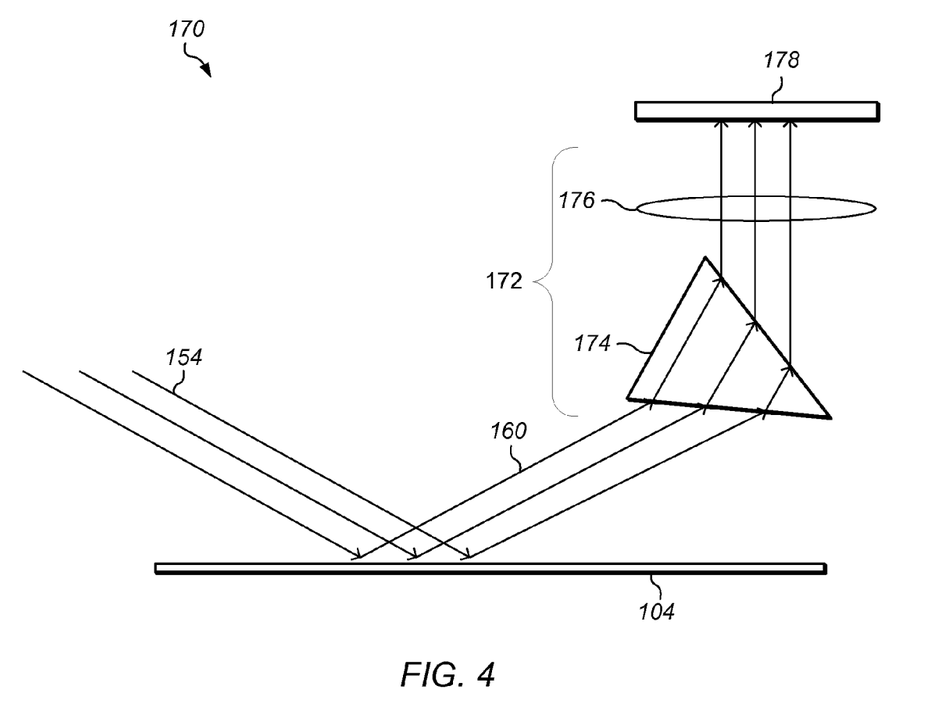
FIG. 4 depicts a representation of an embodiment of a scatterometer using oblique illumination.
Figure 5:
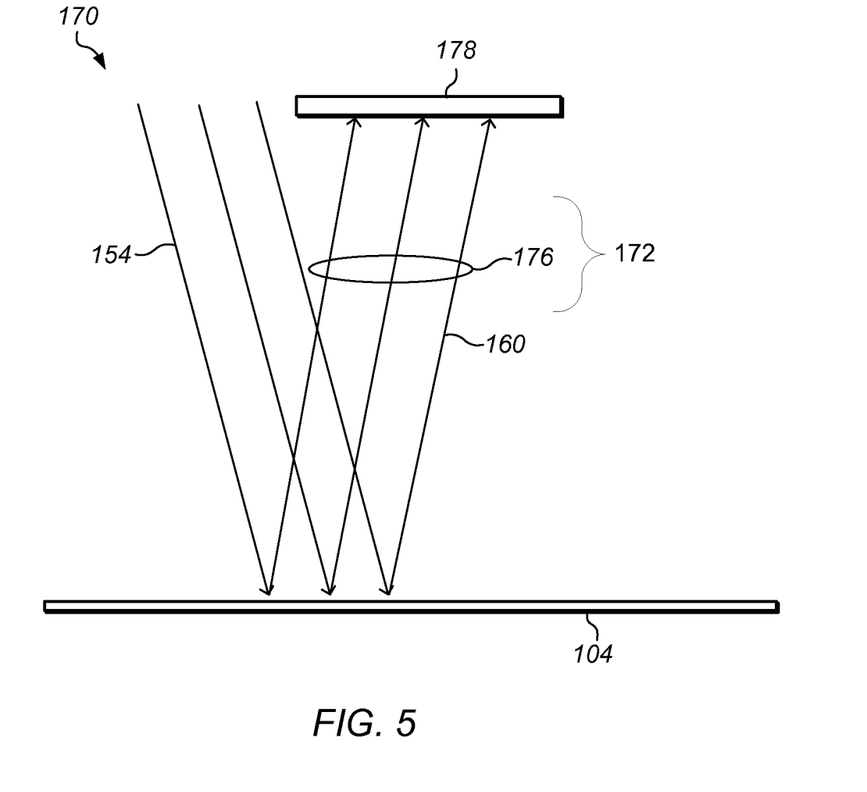
FIG. 5 depicts a representation of another embodiment of a scatterometer using normal illumination.

In certain embodiments, optical scanning system 150 includes a scatterometer that is capable of simultaneously collecting and simultaneously analyzing data from multiple adjacent points. The scatterometer may collect and analyze data from a sample without skipping any areas on the sample. In certain embodiments, the scatterometer includes imaging collection optics and a multi-channel detector or sensor. FIG. 4 depicts a representation of an embodiment of scatterometer 170 using oblique illumination. FIG. 5 depicts a representation of another embodiment of scatterometer 170 using normal illumination. Scatterometer 170 may, for example, be used in an optical scanning system (e.g., optical scanning system 150 shown in FIG. 3) and/or with a moving wafer positioning system 100 (e.g., moving wafer positioning system 100 or moving wafer positioning system 100' shown in FIGS. 1 and 2). In some embodiments, scatterometer 170 is used in a point-to-point optical scanning system.

In certain embodiments, scatterometer includes incident light 154 incident on sample 104. Incident light 154 may include illumination that substantially illuminates all pixels to be imaged by scatterometer 170. Incident light 154 may be provided by, for example, a mode-locked laser or broadband light source in combination with an oblique illumination system, shown in FIG. 4, or a normal (or close to normal) illumination system, shown in FIG. 5. In certain embodiments, incident light 154 has a flat top intensity profile in a long dimension (e.g., x-direction) and a Gaussian profile in a short dimension (e.g., y-direction).

Reflection from sample 104 produces reflected light 160. Reflected light 160 may be collected using collection imaging optics 172. In certain embodiments, collection imaging optics 172 includes prism 174 and lens 176 when used with oblique illumination, as shown in FIG. 4. Prism 174, or a similar optical element such as a variable-over-image-plane optical delay subsystem, may be used to recover the perpendicularity of the image plane to the optical axis in reflected light 160 if the light is reflected at an oblique angle (obliquely) from sample 104.

In certain embodiments, collection imaging optics 172 includes lens 176 when used with normal, or close to normal, illumination, as shown in FIG. 5. When normal, or close to normal illumination is used, there is no need to recover the perpendicularity of the image plane to the optical axis and thus prism 174 or another similar optical element may not be needed (assuming the depth of focus of collection imaging optics 172 is sufficient to keep all points on sample 104 in focus).

Lens 176 may include one or more lenses or optical surfaces that image the surface of sample 104 on sensor 178. The resolvable (pixel) size on sample 104 may be defined by the resolution of collection imaging optics 172, magnification, and pixel size in sensor 178.

Sensor 178 may be a one-dimensional (1D) or two-dimensional (2D) multi-pixel sensor. For a 2D sensor, an x-direction of the sensor may correspond to a long dimension of the illumination line to resolve multiple points on sample 104. A y-direction of the sensor may provide information about polarization of reflected light 160 by having polarizers of desired orientation covering portions of the sensor. In some embodiments, sensor 178 has an internal optical path that includes diffraction grating. The diffraction grating may be used to map the spectrum of incoming light into the y-direction of the sensor, which may be useful for fluorescence measurements.

Sensor 178 may be capable of collecting and providing information about some or all elements of a polarization matrix (e.g., a Mueller polarization matrix). Elements that may be provided include, but are not limited to, polarized and unpolarized reflectivity and spectroscopic ellipsometry data. In certain embodiments, sensor 178 includes an intensity detector. The intensity detector may be used for measurements of reflectivity at a single length. Measurements of reflectivity may include multiple pixels in either single (1D) or two (2D) directions. In certain embodiments, sensor 178 includes a single or multiple imaging spectrometer. The imaging spectrometer may include an entrance point for each image that is a slit (e.g., an entrance slit). In certain embodiments, the slit is oriented parallel to the long dimension of the illumination line. Each point of the slit may be transformed in an orthogonal-to-slit direction into a series of wavelength-specific points. Transformation may be performed using, for example, a flat diffraction grating, a prism, or a similar diffractive element.

In certain embodiments, scatterometer 170 includes a computer system with software. The computer system may be used to process and analyze data collected in sensor 178. Scatterometer 170 provides the ability to process, in parallel, specular reflectance information from multiple adjacent locations on sample 104. Being able to process specular reflectance information from multiple adjacent locations in parallel reduces the requirements on illumination in the optical scanning system as there is no need for a small illumination spot. Processing specular reflectance information from multiple adjacent locations also provides improved resolution and sensitivity at higher throughput (e.g., between about 20 wph and about 100 wph). Scatterometer 170 may be used to detect surface defects such as scratches. In some embodiments, additional analysis is used to ascertain the types of surface defects detected. In certain embodiments, scatterometer 170 is used to measure film thickness and dispersion coefficients (n and k) at the higher throughput. In some embodiments, additional analysis is used to provide autofocus information.

It is to be understood the invention is not limited to particular systems described which may, of course, vary. It is also to be understood that the terminology used herein is for the purpose of describing particular embodiments only, and is not intended to be limiting. As used in this specification, the singular forms "a", "an" and "the" include plural referents unless the content clearly indicates otherwise. Thus, for example, reference to "a lens" includes a combination of two or more lenses and reference to "a light" includes mixtures of lights.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:
1. An optical scanning system, comprising:
a light source configured to provide light towards a sample, wherein the light source provides the light to the sample with a moving optical beam spot;
a spectrometer configured to collect light reflected from the sample; and
a moving sample positioning stage that supports the sample during an optical measurement of the sample using the light source and the spectrometer, wherein the moving sample positioning stage rotates the sample in at least one direction while reflected light is being collected during the optical measurement of the sample;

wherein the moving optical beam spot is rotated synchronously with the sample while reflected light is being collected during the optical measurement such that the moving optical beam spot rotates as the sample rotates and the moving optical beam spot illuminates a specific location on the sample during the optical measurement; and wherein the spectrometer collects reflected light data from the sample during the optical measurement.

2. The system of claim 1, further comprising a continuous auto-focus system for maintaining focus of the light on the sample during the optical measurement of the sample.

3. The system of claim 1, wherein the sample is moved a distance larger than an optical beam spot size of the light on the sample during the optical measurement.

4. The system of claim 1, further comprising a time-delay integration sensor, wherein the time-delay integration sensor temporarily freezes the optical beam spot at one or more locations on the sample while the sample moves during the optical measurement.

5. The system of claim 1, wherein the sample comprises a semiconductor wafer.

6. A method for providing an optical measurement from a sample, comprising:

providing light from a light source towards a sample, wherein the light source provides the light to the sample with a moving optical beam spot;

collecting light reflected from the sample using a spectrometer;

obtaining an optical measurement of the sample using the light source and the spectrometer;

rotating the sample in at least one direction while reflected light is being collected during the optical measurement by moving a sample positioning stage that supports the sample;

rotating the moving optical beam spot synchronously with the sample while reflected light is being collected during the optical measurement such that the moving optical beam spots rotates as the sample rotates and the moving optical beam spot illuminates a specific location on the sample during the optical measurement; and collecting reflected light data from the specific location on the sample during the optical measurement.

7. The method of claim 6, further comprising maintaining focus of the light on the sample during the optical measurement of the sample.

8. The method of claim 6, further comprising moving the sample a distance larger than an optical beam spot size of the light on the sample during the optical measurement.

\* \* \* \* \*